United States Patent
Kalesse et al.

(10) Patent No.: US 8,853,249 B2
(45) Date of Patent: Oct. 7, 2014

(54) METHOD FOR PRODUCING INTERMEDIATES FOR THE PRODUCTION OF MACROCYCLES THAT ARE INHIBITORS OF THE PROTEASOMIC DEGRADATION OF P27, SUCH AS ARGYRIN AND DERIVATIVES THEREOF

(75) Inventors: Markus Kalesse, Burgdorf (DE); Ulrike Eggert, Hannover (DE)

(73) Assignees: Helmholtz-Zentrum für Infektionsforschungs GmbH, Braunschweig (DE); Medizinische Hochschule Hannover, Hannover (DE); Gottfried Wilhelm Leibniz Universität, Hannover (DE)

( * ) Notice: Subject to any disclaimer, the term of this patent is extended or adjusted under 35 U.S.C. 154(b) by 161 days.

(21) Appl. No.: 13/513,128

(22) PCT Filed: Dec. 14, 2010

(86) PCT No.: PCT/EP2010/069594
§ 371 (c)(1),
(2), (4) Date: Aug. 7, 2012

(87) PCT Pub. No.: WO2011/073173
PCT Pub. Date: Jun. 23, 2011

(65) Prior Publication Data
US 2012/0295941 A1      Nov. 22, 2012

Related U.S. Application Data

(60) Provisional application No. 61/287,097, filed on Dec. 14, 2009.

(51) Int. Cl.
*A61K 31/429* (2006.01)
*C07D 513/08* (2006.01)
*C07D 209/20* (2006.01)
*C07B 53/00* (2006.01)

(52) U.S. Cl.
CPC .............. *C07B 53/00* (2013.01); *C07D 209/20* (2013.01); *C07D 513/08* (2013.01)
USPC .......................... 514/368; 548/497; 540/460

(58) Field of Classification Search
USPC ................ 514/368; 548/497; 540/460
See application file for complete search history.

(56) References Cited

U.S. PATENT DOCUMENTS

2011/0311564 A1 * 12/2011 Kalesse et al. ............. 424/185.1

FOREIGN PATENT DOCUMENTS

EP          2138507 A1     12/2009

OTHER PUBLICATIONS

Liu, D. and Zhang, X. "Practical P-Chiral Phosphane Ligand for Rh-Catalyzed Asymmetric Hydrogenation" *Eur. J. Org. Chem*, 2005, pp. 646-649.
Takahashi, H. and Achiwa, K. Efficient Asymmetric Hydrogenations of (Z)-2-Acetamidoacrylic Acid Derivatives with the Cationic Rhodium Complex of (2S,4S)-MOD-BPPM[1]), *Chemistry Letters*, 1989, pp. 305-308.

* cited by examiner

*Primary Examiner* — James O Wilson
*Assistant Examiner* — Oluwafemi Masha
(74) *Attorney, Agent, or Firm* — Saliwanchik, Lloyd & Eisenschenk

(57) ABSTRACT

The present invention relates to an improved method for the synthesis of particular macrocycles that are inhibitors of the proteasomic degradation of p27, in particular argyrin and derivatives thereof.

8 Claims, No Drawings

METHOD FOR PRODUCING INTERMEDIATES FOR THE PRODUCTION OF MACROCYCLES THAT ARE INHIBITORS OF THE PROTEASOMIC DEGRADATION OF P27, SUCH AS ARGYRIN AND DERIVATIVES THEREOF

CROSS REFERENCE TO A RELATED APPLICATION

This application is a National Stage Application of International Application Number PCT/EP2010/069594, filed Dec. 14, 2010; which claims the benefit of U.S. Provisional Application Ser. No. 61/286,097, filed. Dec. 14, 2009; all of which are incorporated herein by reference in their entirety.

DESCRIPTION

The present invention relates to an improved method for the synthesis of particular macrocycles that are inhibitors of the proteasomic degradation of p27, in particular argyrin and derivatives thereof.

BACKGROUND OF THE INVENTION

Reduction in the cellular levels of the cyclin kinase inhibitor p27$^{kip1}$ is frequently found in many human cancers and correlate directly with patient prognosis (Philipp-Staheli, J., Payne, S. R. and Kemp, C. J. p27(Kip1): regulation and function of a haplo-insufficient tumour suppressor and its misregulation in cancer. *Exp Cell Res* 264, 148-68 (2001)). Specifically ubiquitin dependent proteasomal turnover has been shown to cause reduced p27 expression in many human cancers (Loda, M. et al. Increased proteasome-dependent degradation of the cyclin dependent kinase inhibitor p27 in aggressive colorectal carcinomas. Nat Med 3, 231-4 (1997)).

GB 2,367,553 discloses pharmaceutically active macrocycles ("argyrines") and respective pharmaceutical preparations for the treatment of autoimmune diseases, the induction of immunotolerance or the treatment of bacterial infections. Sasse F et al. (in Sasse F, Steinmetz H, Schupp T, Petersen F, Memmert K, Hofmann H, Heusser C, Brinkmann V, von Matt P, Hofle G, Reichenbach H. Argyrins, immunosuppressive cyclic peptides from myxobacteria. I. Production, isolation, physico-chemical and biological properties. J Antibiot (Tokyo). 2002 June; 55 (6):543-51.) describe the production of a group of cyclic peptides called argyrins, as well as some of their biological properties. Vollbrecht et al. (in Vollbrecht L, Steinmetz H, Hofle G, Oberer, L, Rihs G, Bovermann G, and von Matt P. Argyrins, immunosuppressive cyclic peptides from myxobacteria. II. Structure elucidation and stereochemistry. J Antibiot (Tokyo). 2002 August; 55 (8):715-721.) describe the structure of said cyclic peptides. Argyrines A-H can be obtained from the myxobacterium *Aarchangium gephyra*.

Similarly, Ley et al. (in Ley SV, Priour A, Heusser C. Total synthesis of the cyclic heptapeptide Argyrin B: a new potent inhibitor of T-cell independent antibody formation. Org Lett. 2002 Mar. 7; 4 (5):711-4.) describe the synthesis of argyrin B and its function as inhibitor of antibody formation.

EP1964560 describes the use of the macrocycles of GB 2,367,553 for the production of a medicament for the treatment of cancer in a subject.

WO/2010/006682 "Method for producing intermediates for the production of novel macrocycles that are inhibitors of the proteasomic degradation of p27, such as argyrin and derivatives thereof, and uses of said macrocycles", which is herewith incorporated by reference in its entirety, describes intermediates for the production of macrocycles that are inhibitors of the proteasomic degradation of p27, such as argyrin and derivatives thereof, as well as methods for the production and biological activity of said macrocycles.

Argyrines and related macrocycles are therefore interesting candidates for the further development of medicaments for a treatment in a variety of conditions, such as the induction of immunotolerance, autoimmune diseases, bacterial infections, and proliferative diseases, such as cancers.

Nevertheless, the full exploitation of the pharmaceutical potential of argyrines and their related derivatives is difficult because of their relatively complex chemical structure, which requires laborious efforts to isolate sufficient amounts of the compounds (e.g. from micro-organisms), and limits the number of effective compounds of this family that are readily available for studies and treatment. It is particularly difficult to readily produce stereoselective forms of argyrines in a sufficient amounts and purities.

It is therefore an object of the present invention to provide improved methods for the production of compounds of the family of argyrines, and respective intermediates.

According to a first aspect of the present invention, the above object is solved by a method for producing optionally protected L-4-methoxytryptophane comprising the synthesis of the protected L-4-methoxytryptophanemethylester according to formula 2

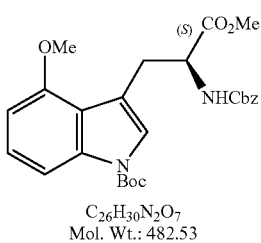

$C_{26}H_{30}N_2O_7$
Mol. Wt.: 482.53 comprising an asymmetric hydrogenation using [1S,1S',2R,2R'-DuanPhos Rh(cod)]BF$_4$ as a catalyst. According to a second aspect of the present invention, the above object is further solved by a method for producing optionally protected D-4-methoxytryptophane comprising the synthesis of the protected D-4-methoxytryptophanemethylester according to the formula

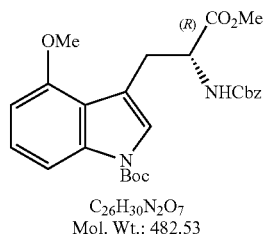

$C_{26}H_{30}N_2O_7$
Mol. Wt.: 482.53 comprising an asymmetric hydrogenation using [1R,1R',2S,2S'-DuanPhos Rh(cod)]BF$_4$ as a catalyst.

Thus, preferred is a method for producing stereoselective optionally protected D-4- or L-4-methoxytryptophane using catalytic asymmetric hydrogenation, wherein the catalyst is prepared from [Rh(cod)$_2$]BF$_4$ and 1S,1S',2R,2R'-DuanPhos or 1R,1R',2S,2S'-DuanPhos respectively. Preferred is a method, wherein the enantiomeric excess is at least 97% ee, and 98% ee, respectively. Most preferred is more than 99% ee.

Initially, 4-methoxy-L-tryptophane could only be produced through an enzymatic resolution (Ley, S. V.; Priour, A. *Eur. J. Org. Chem.* 2002, 3995-4004; Ley, S. V.; Priour, A.; Heusser, C. *Org. Lett.* 2002, 4, 711-714). The yields that can be obtained in principal can never exceed 50%. In practice, only yields of as low as between 10 and 40% were reached. PCT/EP2009/004526 describes a synthesis that can only be achieved with a selectivity of 90% ee. It was now surprisingly found that, using the hydrogenation catalysts as presented herein, a markedly improvement could be achieved in the asymmetric hydration and therefore both in the synthesis of the methoxytryptophane element and the overall synthesis of argyrines.

Thus, further preferred is a method for producing a macrocycle compound according to the present invention or 4-methoxy-L- or 4-methoxy-D-tryptophane as above, wherein the synthesis is performed without the uses of enzymes.

Even further preferred is a method for producing a macrocycle compound according to the present invention, wherein said synthesis comprises a solid phase synthesis. More preferably, said synthesis comprises solid phase peptide synthesis of a linear precursor involving the above mentioned amino acid. The solid phase synthesis allows elimination to produce the exo-methylen group after ring closure.

In the method for producing a macrocycle compound according to the present invention said asymmetric hydrogenation can be carried out under a pressure of between 1 and 100 bar, preferably between 1 and 20 bar, and most preferably 1 to 10 bar. Preferred is a method for producing a macrocycle compound according to the present invention, wherein said asymmetric hydrogenation is carried out at a temperature of between 15° C. and 100° C. Also preferred is a method for producing a macrocycle compound according to the present invention, wherein said asymmetric hydrogenation is carried out using alcohol, and preferably methanol, as a solvent. Advantageously, the present method provides the tryptophane element(s) with a very high specific ee-value. This simplifies the purification at the end of the synthesis and increases the yield(s).

According to a third aspect of the present invention, the above object is solved by a method for producing a macrocycle compound according to the following general formula (I)

(I)

wherein $R^1$ and $R^2$ independently are hydrogen, $C_1$-$C_4$ alkyl which is unsubstituted or substituted by OH, or $C_1$-$C_4$ alkoxy; $R^3$ is hydrogen, $C_1$-$C_4$ alkoxy, $C_1$-$C_8$ alkyl which is unsubstituted or substituted by OH or OR, wherein R is selected from hydrogen, $C_1$-$C_4$ alkyl, aryl or acetyl, or $C_1$-$C_4$ alkoxy, $R^4$ is hydrogen, halogen, $C_1$-$C_4$ alkyl which is unsubstituted or substituted by OH, or $C_1$-$C_4$ alkoxy; $R^5$ is hydrogen or halogen; $R^6$ is hydrogen or $C_1$-$C_4$ alkyl; $R^7$ is hydrogen or $C_1$-$C_4$ alkyl which is unsubstituted or substituted by OH, or $C_1$-$C_4$ alkoxy; and X is C=$CH_2$ or $CHR^8$ wherein $R^8$ is $C_1$-$C_4$ alkyl which is unsubstituted or substituted by —S—$C_1$-$C_4$ alkyl, and stereoisomers and pharmaceutically acceptable salts thereof, comprising a synthesis of optionally protected 4-methoxy-tryptophane according to the present invention. Preferred is a method as above, wherein $R^7$ is hydrogen or $C_1$-$C_4$ alkyl which is unsubstituted or substituted by OH, or $C_1$-$C_4$ alkoxy; and X is C=$CH_2$ or CHR' wherein $R^7$ is $C_1$-$C_4$ alkyl which is unsubstituted or substituted by —S—$C_1$-$C_4$ alkyl. More preferred is a method as above, wherein if $R^1$ is not hydrogen, X must be $CH_2$.

Further preferred is a method for producing a macrocycle compound according to the present invention, wherein said macrocycle compound is selected from an argyrin, such as argyrin A-F, B/F, and Ala alpha and Ala beta, and isolated stereoisomers thereof. Particularly preferred is a method of the present invention as above for producing a macrocycle compound that is selected from the following formulae Argyrin B/F Argyrin Ala beta

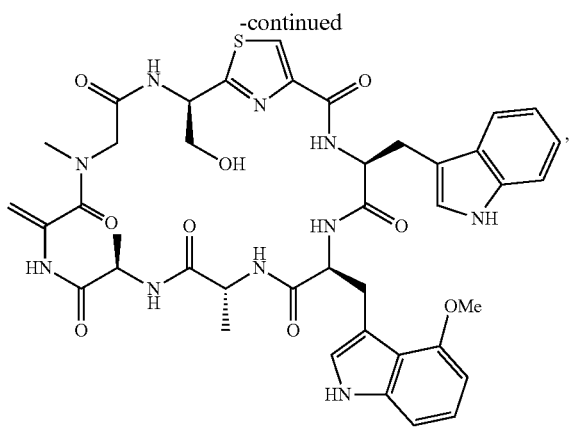

Argyrin Ala alpha and pharmaceutically acceptable salts thereof.

Further preferred is a method for producing a macrocycle compound according to the present invention further comprising the step of a chemical modification of said compound. In this case, the compound will function as a so-called "lead-structure" which is further subjected to chemical modifications which are then screened for their effectiveness to increase the amount and/or biological activity of p27 in one or more subsequent screening methods as known. Modification can be effected by a variety of methods known in the art, which include, without limitation, the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or isopentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group. Furthermore, additional peptide groups could be added to the molecule, such as single amino acids, dipeptides, tripeptides, and so on.

Yet another aspect of the present invention is directed to a method for producing a pharmaceutical composition, comprising the method for producing a macrocycle compound according to the present invention as herein, and admixing said macrocycle compound together with pharmaceutically acceptable carriers and/or excipients. Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Administration of an agent, e.g., a compound can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is then directed to a pharmaceutical composition that is produced according to the method as above.

Another aspect of the present invention is the use of a pharmaceutical composition produced according to the present invention for the treatment of a disease or condition selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer. Yet another aspect of the present invention is the use of a compound according to the present invention for the production of a medicament for the treatment of a disease or condition selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer.

The biological effects of different argyrin-derivatives as synthesized was tested as described in the examples section of WO/2010/006682 (herewith incorporated by reference), and were found to be essentially identical. Thus, compounds as produced according to the present method are effective in the treatment of a disease or condition selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer.

It is assumed that the possibility to synthesize the active compounds in better yields and purities will also improve the effect of respective pharmaceutical compositions, as lower dosages can be used leading to fewer potential side effects. Furthermore, a more straight forward synthesis improves the safety of a respectively produced medicament, as, for example, fewer mistakes can be made in the production process.

The following examples merely serve to illustrate the invention and should not be construed to restrict the scope of the invention to the particular embodiments of the invention described in the examples. For the purposes of the present invention, all references as cited herein are hereby incorporated herein by reference in their entireties. It should be understood that the following syntheses can be readily modified by the person of skill in order to synthesize other derivatives of the present invention based on the strategies as provided.

EXAMPLES

1. Synthesis of 4-Methoxy-L-tryptophane (2)

In order to avoid the fundamental problems in synthesizing (2) an optimized stereoselective catalytic hydrogenation was established as a new, efficient and economic synthesis method.

General Production of the Catalyst

For the production of the hydrogenation catalyst DuanPhos (70 mg, 0.18 mmol) was dissolved in THF (1 ml) and [Rh(cod)$_2$]BF$_4$ (71 mg, 0.175 mmol) in THF (3 ml) was added. The solution was stirred for 30 min and subsequently Et$_2$O (12.5 ml) was added. The residue was filtered off, washed with Et$_2$O, and residual solvents were removed in vacuo.

Hydrogenation (S-enatiomer)

The catalyst (1.6 mg) as produced from 1S,1S',2R,2R'-DuanPhos and [Rh(cod)$_2$]BF$_4$ is dissolved in MeOH (3 mL) and 96 mg of the educt 1 dissolved MeOH (1 mL) are added. The reaction mixture is hydrogenated 1 d at 10 bar. After removal of the solvent under reduced pressure the catalyst is removed using column filtration (MTBE/PE, 1:1). The reaction product (2) is obtained in quantitative yield with an enantiomeric excess of 98.7%.

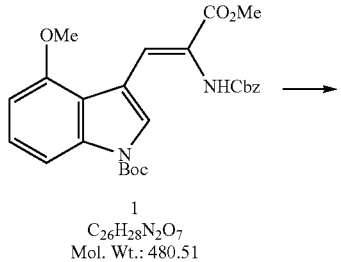

1
C$_{26}$H$_{28}$N$_2$O$_7$
Mol. Wt.: 480.51

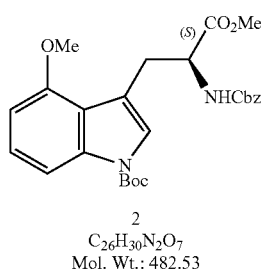

2
C$_{26}$H$_{30}$N$_2$O$_7$
Mol. Wt.: 482.53

Ligands for Catalytic Reaction

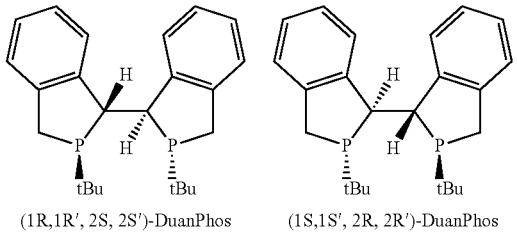

(1R,1R', 2S, 2S')-DuanPhos    (1S,1S', 2R, 2R')-DuanPhos 1S,1S',2R,2R'-DuanPhos ((1S,1'S,2R,2'R)-2,2'-Di-tert-butyl-2,3,2',3'-tetrahydro-1H,1'H(1,1')biisophosphindolyl) and 1R,1R',2S2S'-DuanPhos ((1R,1'R,2S,2'S)-2,2'-Di-tert-butyl-2,3,2',3'-tetrahydro-1H,1'H-(1,1')Nisophosphindolyl) are commercially available, e.g. from Sigma-Aldrich, St. Louis, Mo.

Synthesis of the Second (R-)enantiomer

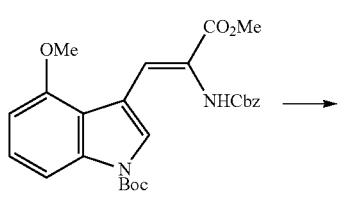

C$_{26}$H$_{28}$N$_2$O$_7$
Mol. Wt.: 480.51

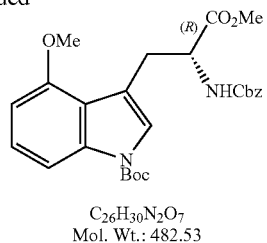

C$_{26}$H$_{30}$N$_2$O$_7$
Mol. Wt.: 482.53

The R-enantiomer of the tryptophane module is produced in accordance with the above-described synthesis-protocol using 1R,1R',2S,2S'-DuanPhos.

|         | MW     | d    | eq     | mmol    |
|---------|--------|------|--------|---------|
| Olefin  | 480.51 | 1    | 0.2    | 96 mg   |
| Cat.    | 788.53 | 0.01 | 0.0002 | 1.6 mg  |
| MeOH    |        |      |        | 4 ml    |

Yield: quant. % ee: 97.6

The enantioselectivity, as well as the absolute configuration was determined with the Mosher-method following Cbz-deprotection.

Synthesis of Mosher-amide 11

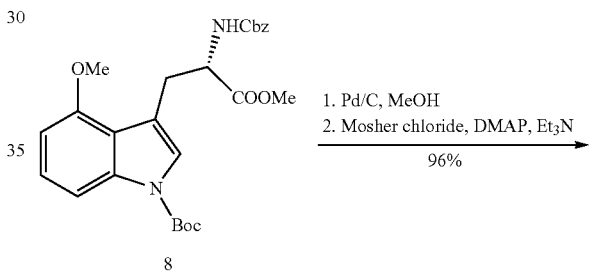

8

1. Pd/C, MeOH
2. Mosher chloride, DMAP, Et$_3$N
96%

11

Palladium on charcoal (100 mg, 10% weight) was added to a solution of N$^\alpha$-Cbz-N$^{Ind}$-Boc-L-Trp-OMe 8 (20 mg, 0.04 mmol) in methanol (1 ml). The reaction mixture was purged with hydrogen three times and stirred for 12 hours at room temperature. The suspension was filtered through a plug of Celite®, washed with methanol (2×3 mL) and concentrated. The amine was used directly in the next step.

To a solution of the amine (5 mg, 14 µmol) in dichloromethane (1 mL) was added at room temperature successively triethylamine (16 µL, 115 µmol), DMAP (3.2 mg, 26 µmol), (S)-Mosher chloride (11 µL, 58 µmol). The mixture was stirred at room temperature for 3 hours and quenched with ethyl acetate (10 mL). The mixture was washed successively with saturated aqueous NaHSO$_4$ (5 mL), 1 N NaOH (5 mL) and saturated aqueous NaHCO$_3$ (2×5 mL). The organic phase was dried over MgSO$_4$, filtered and concentrated under reduced pressure. The crude residue was purified by flash chromatography to afford the corresponding Mosher ester 11 (8 mg, 14 µmol, 96%).

Rf=0.18 (Ethyl acetate/n-hexane 1:3);

$^1$H-NMR (400 MHz, CDCl$_3$): δ=7.83 (d, J=6.8 Hz, 1 H), 7.79 (d, 8.5 Hz, 1 H), 7.60-7.53 (m, 2H), 7.43-7.36 (m, 3 H), 7.33 (s, 1 H), 7.25-7.21 (m, 1 H), 6.67 (d, J=7.9 Hz, 1 H), 4.78-4.70 (m, 1 H), 3.77 (s, 3 H), 3.75 (s, 3 H), 3.43-3.35 (m, 1 H), 3.28 (dd, J=14.3, 9.9 Hz, 1 H), 2.92 (d, J=1.4 Hz, 3 H), 1.66 (s, 9 H).

$^{13}$C-NMR (100 MHz, CDCl$_3$): δ=171.8, 166.9, 153.5, 149.5, 133.0, 129.7, 129.6, 128.6, 128.3, 128.2, 125.6, 125.2, 123.6, 119.6, 115.3, 108.9, 103.3, 84.0, 77.4, 55.2, 54.9, 52.4, 28.3, 28.0.

HRMS (ESI) calculated for C$_{28}$H$_{31}$N$_2$O$_7$F$_3$Na ([M+Na]$^+$): 587.1981, found: 587.1982.

Synthesis of Cbz-protected Methoxytryptophane

Trifluoroacetic acid (0.5 mL) was added dropwise to a solution of methoxytryptophane (95 mg, 0.20 mmol) in dichloromethane (4 mL) at 0° C. The reaction mixture was stirred for 3.5 hours at room temperature. The solution was concentrated by co-evaporation with toluene (3×5 mL) and the resulting deprotected tryptophane was used directly in the next step.

A 0.5 N aqueous solution of LiOH (0.8 mL, 0 4 mmol) was added to a solution of the deprotected tryptophane in tetrahydrofurane/methanol/water (7:1.3:4 mL) at 0° C. The reaction mixture was warmed to room temperature and stirred for 2 hours. The solution was partitioned between 0.1 N aqueous HCl (15 mL) and dichloromethane (15 mL). The aqueous layer was extracted with dichloromethane (2×15 mL) and the organic layers were combined, dried (Na$_2$SO$_4$) and concentrated. The residue was purified by column chromatography (dichloromethane with a gradient of 1 to 5% methanol) to give 51 mg of Cbz-protected methoxytryptophane 2 as a white solid (0.14 mmol, 70%, 2 steps).

Rf=0.27 (Ethyl acetate/n-hexane 3:1, with 1% acetic acid);

[α]$_{589}^{20}$=−44.3 (c=0.3, MeOH)

$^1$H-NMR (400 MHz, [D6]DMSO, 60° C.): δ=10.75 (br, s, 1H), 7.41 (d, J=8 Hz, 1H), 7.24-7.34(m, 5H), 6.9-7.2 (m, 3H), 6.44 (d, J=7 Hz, 1H), 4.95 (m, 2H), 4.30 (m, 1H), 3.83 (s, 3H), 3.35(dd, J=14, 4 Hz, 1H), 2.95 (dd, J=14, 10 Hz, 1H).

2. Synthesis and in Particular Solid Phase Synthesis of Argyrins and Functional Assays The synthesis of argyrins comprising the tryptophane amino acid production step as above, in particular comprising a solid phase peptide synthesis technique allowing for the rapid and efficient assembly of peptides through automation, can be performed as described in the examples section of WO/2010/006682 (PCT/EP2009/004526, herewith incorporated by reference).

The biological effects of different argyrin-derivatives as synthesized was tested as described in the examples section of WO/2010/006682 (herewith incorporated by reference), and were found to be essentially identical. Thus, compounds as produced according to the present method are effective in the treatment of a disease or condition selected from the induction of immunotolerance, autoimmune diseases, bacterial infections, and proliferative diseases, such as psoriasis or cancers, such as breast cancer, hepatocellular carcinoma, myeloma, cervix carcinoma, lung carcinoma, and colon cancer.

It is assumed that the possibility to synthesize the active compounds in better yields and purities will also improve the effect of respective pharmaceutical compositions, as lower dosages can be used leading to fewer potential side effects. Furthermore, a more straight forward synthesis improves the safety of a respectively produced medicament, as, for example, fewer mistakes can be made in the production process.

The invention claimed is:

1. A method for producing a macrocycle compound according to the following general formula (I)

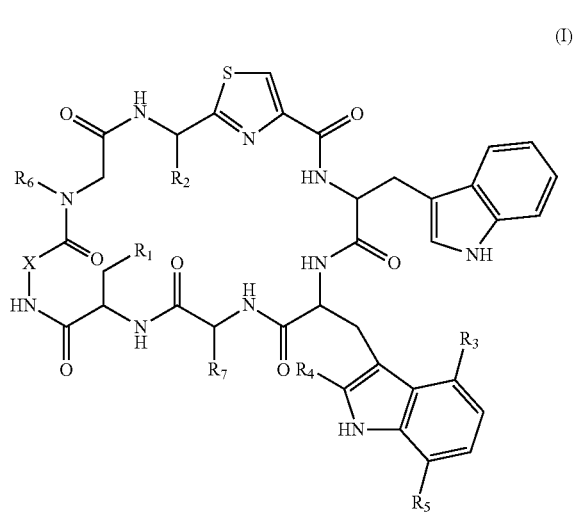

wherein

R$^1$ and R$^2$ independently are hydrogen, C$_1$-C$_4$ alkyl which is unsubstituted or substituted by OH, or C$_1$-C$_4$ alkoxy;

R$^3$ is hydrogen, C$_1$-C$_4$ alkoxy, C$_1$-C$_8$ alkyl which is unsubstituted or substituted by OH or OR, wherein R is selected from hydrogen, C$_1$-C$_4$ alkyl, aryl or acetyl, or C$_1$-C$_4$ alkoxy, R$^4$ is hydrogen, halogen, C$_1$-C$_4$ alkyl which is unsubstituted or substituted by OH, or C$_1$-C$_4$ alkoxy;

R$^5$ is hydrogen or halogen;

R$^6$ is hydrogen or C$_1$-C$_1$ alkyl;

R$^7$ is hydrogen or C$_1$-C$_4$ alkyl which is unsubstituted or substituted by OH, or C$_1$-C$_4$ alkoxy; and X is C=CH$_2$ or CHR$^8$ wherein R$^8$ is C$_1$-C$_4$ alkyl which is unsubstituted or substituted by —S—C$_1$-C$_4$ alkyl, and stereoisomers and pharmaceutically acceptable salts thereof, comprising a synthesis of optionally protected 4-methoxy-tryptophan according to formula 2:

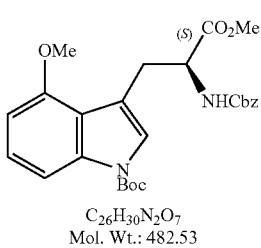

or the formula:

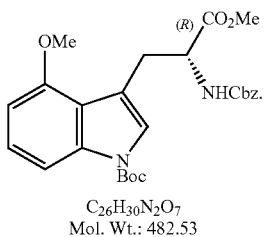

C$_{26}$H$_{30}$N$_2$O$_7$
Mol. Wt.: 482.53

2. The method for producing a macrocycle compound according to claim 1, wherein said synthesis comprises a solid phase synthesis.

3. The method for producing a macrocycle compound according to claim 1 wherein said asymmetric hydrogenation is carried out under a pressure of between 1 and 100 bar.

4. The method for producing a macrocycle compound according to claim 1, wherein said asymmetric hydrogenation is carried out at a temperature of between 15° C. and 100° C.

5. The method for producing a macrocycle compound according to claim 1, wherein the asymmetric hydrogenation is carried out using alcohol as a solvent.

6. The method for producing a macrocycle compound according to claim 1, wherein said macrocycle compound is selected from an argyrin, Ala-alpha and Ala-beta, and isolated stereoisomers thereof.

7. The method for producing a macrocycle compound according to claim 1, wherein the synthesis comprises solid phase peptide synthesis.

8. A method for producing a pharmaceutical composition, comprising the method for producing a macrocycle compound according to claim 1, and admixing said macrocycle compound together with pharmaceutically acceptable carriers and/or excipients.

* * * * *

UNITED STATES PATENT AND TRADEMARK OFFICE
CERTIFICATE OF CORRECTION

PATENT NO. : 8,853,249 B2
APPLICATION NO. : 13/513128
DATED : October 7, 2014
INVENTOR(S) : Markus Kalesse et al.

It is certified that error appears in the above-identified patent and that said Letters Patent is hereby corrected as shown below:

In the Specification

Column 7,
Line 52, "Nisophosphindolyl" should read -- biisophosphindolyl --.

Signed and Sealed this
Fourteenth Day of April, 2015

Michelle K. Lee
*Director of the United States Patent and Trademark Office*